United States Patent
Agee et al.

(10) Patent No.: US 6,277,894 B1
(45) Date of Patent: Aug. 21, 2001

(54) SYSTEM AND METHOD FOR CONVERTING LIGHT HYDROCARBONS INTO HEAVIER HYDROCARBONS WITH A PLURALITY OF SYNTHESIS GAS SUBSYSTEMS

(75) Inventors: Kenneth L. Agee, Bixby; Mark A. Agee, Tulsa, both of OK (US)

(73) Assignee: Syntroleum Corporation, Tulsa, OK (US)

( * ) Notice: Subject to any disclaimer, the term of this patent is extended or adjusted under 35 U.S.C. 154(b) by 0 days.

(21) Appl. No.: 09/538,609

(22) Filed: Mar. 29, 2000

Related U.S. Application Data (60) Provisional application No. 60/126,996, filed on Mar. 30, 1999.

(51) Int. Cl.[7] ............................................. C07C 27/00
(52) U.S. Cl. ........................ 518/700; 518/702; 518/703; 518/704
(58) Field of Search .................... 518/700, 702, 518/703, 704

(56) References Cited

U.S. PATENT DOCUMENTS

| | | | |
|---|---|---|---|
| 4,833,170 | 5/1989 | Agee | 518/703 |
| 4,973,453 | 11/1990 | Agee | 422/190 |
| 5,490,377 | 2/1996 | Janes | 60/39.12 |
| 5,666,800 | 9/1997 | Sorenson et al. | 60/39.02 |
| 5,694,761 | 12/1997 | Griffin, Jr. | 69/39.05 |
| 5,733,941 | 3/1998 | Waycuilis | 518/703 |
| 5,861,441 | 1/1999 | Waycuilis | 518/703 |
| 5,973,631 | 10/1999 | McCullen et al. | 341/144 |
| 5,980,840 | 11/1999 | Kleefisch et al. | 422/211 |

FOREIGN PATENT DOCUMENTS

| | | | |
|---|---|---|---|
| 0748763A1 | 12/1996 | (EP) | C01B/3/36 |
| WO 97/30011 | 8/1997 | (WO) | C07C/7/06 |
| WO 99/19277 | 4/1999 | (WO) | C07C/1/04 |

OTHER PUBLICATIONS

"PFBC clean–coal technology. A new generation of combined–cycle plants to meet the growing world need for clean and cost effective power." ABB Carbon Marketing Department, S–612 82 Finspong, Approximately Feb. 1998.

PCT International Search Report (PCT Rule 44.1), mailed Nov. 2, 2000 re International Application PCT/US00/08371 filed Mar. 29, 2000 (Applicant's reference 062754.0214).

*Primary Examiner*—Sreeni Padmanabhan
*Assistant Examiner*—J. Parsa
(74) *Attorney, Agent, or Firm*—Baker Botts L.L.P.

(57) ABSTRACT

A system and method for converting normally gaseous, light hydrocarbons into heavier, longer-chain hydrocarbons includes a turbine; a first synthesis gas subsystem; a second synthesis gas subsystem that receives thermal energy from the turbine and which preferably includes a steam reformer; and a synthesis subsystem for receiving synthesis gas from the first synthesis gas subsystem and the second synthesis gas subsystem and for producing the heavier hydrocarbons.

A method includes using a plurality of synthesis gas subsystems to prepare synthesis gas for delivery to and conversion in a synthesis subsystem.

5 Claims, 3 Drawing Sheets

SYSTEM AND METHOD FOR CONVERTING LIGHT HYDROCARBONS INTO HEAVIER HYDROCARBONS WITH A PLURALITY OF SYNTHESIS GAS SUBSYSTEMS

RELATED APPLICATION

This application claims the benefit of U.S. provisional application Ser. No. 60/126,996, filed Mar. 30, 1999, entitled SYSTEM AND METHOD FOR CONVERTING LIGHT HYDROCARBONS INTO HEAVIER HYDROCARBONS WITH A PLURALITY OF SYNTHESIS GAS SUBSYSTEMS.

TECHNICAL FIELD OF THE INVENTION

The present invention relates to synthesis systems and more particularly, to a system and method for converting (e.g., through a Fischer-Tropsch reaction) light hydrocarbons, such as natural gas, into heavier hydrocarbons with a plurality of synthesis gas subsystems.

BACKGROUND OF THE INVENTION

As concerns over pollution caused by traditional fossil fuels increases and as sources of crude oil decrease, there has been increased interest in other sources of energy. One promising source of energy is the synthetic production of fuels, lubricants, and other products from natural gas (referred to at times as gas-to-liquids or GTL) preferably through the Fischer-Tropsch process. See for example U.S. Pat. Nos. 4,883,170 and 4,973,453, which are incorporated by reference herein for all purposes.

A. Introduction to the Fischer Tropsch Process

The synthetic production of hydrocarbons by the catalytic reaction of synthesis gas is well known and is generally referred to as the Fischer-Tropsch reaction. The Fischer-Tropsch process was developed in early part of the $20^{th}$ century in Germany. It was practiced commercially in Germany during World War II and later has been practiced in South Africa.

The Fischer-Tropsch reaction for converting synthesis gas (primarily CO and $H_2$) has been characterized in some instances by the following general reaction:

$$2H_2 + CO \xrightarrow{\text{Catalyst}} -CH_2- + H_2O$$

The hydrocarbon products derived from the Fischer-Tropsch reaction range from some methane to high molecular weight paraffinic waxes containing more than 50 carbon atoms.

Numerous catalysts incorporating active metals, such as iron, cobalt, ruthenium, rhenium, etc., have been used in carrying out the reaction, and both saturated and unsaturated hydrocarbons can be produced. The synthesis reaction is very exothermic and temperature sensitive whereby temperature control is required to maintain a desired hydrocarbon product selectivity.

B. Synthesis Gas Production

Synthesis gas may be made from natural gas, gasified coal, and other sources. A number of basic methods have been employed for producing the synthesis gas ("syngas"), which is substantially carbon monoxide and molecular hydrogen, utilized as feedstock in the Fischer-Tropsch reaction. The numerous methodologies and systems that have been used to prepare synthesis gas include partial oxidation, steam reforming, auto-reforming or autothermal reforming. Both fixed and fluid bed systems have been employed.

The reforming reactions are endothermic and a catalyst containing nickel is often utilized. Partial oxidation (non-catalytic or catalytic) involves sub-stoichiometric combustion of light hydrocarbons such as methane to produce the synthesis gas. The partial oxidation reaction is typically carried out commercially using high purity oxygen.

In some situations these synthesis gas production methods may be combined to form another method. A combination of partial oxidation and steam reforming, known as autothermal reforming, wherein air may be used as the oxygen-containing gas for the partial oxidation reaction has also been used for producing synthesis gas heretofore. Autothermal reforming, the combination of partial oxidation and steam reforming, allows the exothermic heat of the partial oxidation to supply the necessary heat for the endothermic steam reforming reaction. The autothermal reforming process can be carried out in a relatively inexpensive refractory lined carbon steel vessel whereby a relatively lower cost is typically involved.

The autothermal reforming process results in lower hydrogen to carbon monoxide ratio in the synthesis gas than does steam reforming alone. That is, the steam reforming reaction with methane results in a ratio of about 3:1 or higher while the partial oxidation of methane results in a ratio of less than about 2:1—depending upon the extent of the water gas shift reaction. A good ratio for the hydrocarbon synthesis reaction carried out at low or medium pressure (i.e., in the range of about atmospheric to 500 psig) over a cobalt catalyst is about 2:1. When the feed to the autothermal reforming process is a mixture of light shorter-chain hydrocarbons such as a natural gas stream, some form of additional control is desired to maintain the ratio of hydrogen to carbon monoxide in the synthesis gas at the optimum ratio (for cobalt based F-T catalysts) of about 2:1. For this reason steam and/or $CO_2$ may be added to the synthesis gas reactor to adjust the $H_2/CO$ ratio to the desired value with the goal of optimizing the process economics.

C. Improved Economics Desired

It has been a quest for many to improve the economics of processes utilizing the Fischer-Tropsch reaction. Improved economics will allow a wide-scale adoption of the process in numerous sites and for numerous applications. Efforts have been made toward that end, but further improvements are desirable.

SUMMARY OF THE INVENTION

A need has arisen for a system and method for converting light hydrocarbons into heavier hydrocarbons ($C_{5+}$) that addresses disadvantages and problems associated with previously developed systems and methods. According to an aspect of the present invention, a system for converting normally gaseous hydrocarbons into heavier hydrocarbons, which are liquid or solid at standard temperature and pressure, includes: a turbine; a first synthesis gas subsystem; a second synthesis gas subsystem that receives thermal energy from the turbine and which includes a steam reformer; and a synthesis subsystem for receiving synthesis gas from the first synthesis gas subsystem and from the second synthesis gas subsystem and which produce the heavier hydrocarbons.

According to another aspect of the present invention, a method for converting normally gaseous hydrocarbons to heavier hydrocarbons that are normally solid or liquid at standard temperature and pressure is provided that includes the steps of: preparing a synthesis gas in a first synthesis gas unit; providing a steam reformer having a primary reforming zone; providing a turbine having a compressor section, cumbustor, and expansion section; thermally coupling the expansion section of the turbine to the steam reformer to provide at least a portion of the reaction energy required in the steam reformer to produce synthesis gas; preparing a synthesis gas in the steam reformer; delivering the synthesis gas from the first synthesis gas unit and the steam reformer to a synthesis subsystem for conversion to the heavier hydrocarbons. According to another aspect of the present invention, the combustor section of the gas turbine may be combined with the first synthesis gas unit, which may be an autothermal reformer or a steam reformer.

The present invention provides a number of advantages. A few examples follow. A technical advantage of the present invention is that it allows more efficient use of energy in a turbine-powered synthesis system. Another technical advantage of the present invention is that it lowers the nitrogen content in the synthesis gas compared to a straight air-blown autothermal reformer based conversion system.

BRIEF DESCRIPTION OF THE DRAWINGS

For a more complete understanding of the present invention and advantages thereof, reference is now made to the following description taken in conjunction with the accompanying drawings in which like reference numbers indicate like features, and wherein.

DETAILED DESCRIPTION OF THE INVENTION

The preferred embodiment of the present invention and its advantages are best understood by referring to FIGS. 1–6 of the drawings, like numerals being used for like and corresponding parts of the various drawings.

Figure 1:
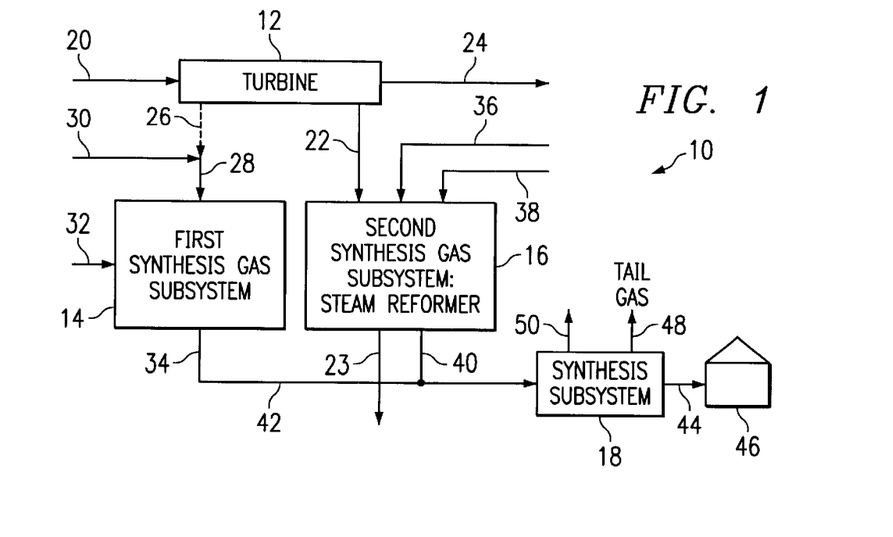
FIG. 1 is a schematic diagram of a conversion system according to one embodiment of the present invention.

Referring to FIG. 1, a system 10 for converting normally gaseous hydrocarbons into heavier hydrocarbons, which are primarily liquid or solid at standard temperature and pressure, is presented. System 10 includes a turbine unit 12, a first synthesis gas subsystem 14, a second synthesis gas subsystem 16, which is preferably a steam reformer, and a synthesis subsystem 18, which reacts synthesis gas to form heavier, longer-chain hydrocarbons (e.g., $C_{5+}$).

Turbine 12 has an air inlet 20 and an exhaust outlet 22. While "air" is referenced in this application, it is to be understood that other oxygen-containing gases might be used as well, e.g., enriched air. Turbine 12 generates mechanical energy that may be used to run additional compressors or to generate electricity or for other uses (e.g, power for plasma synthesis techniques), as is represented by power offtake 24. Turbine 12 may be a gas turbine or a compressor/steam turbine combination. As will be described below, turbine 12 includes a compressed air outlet 26.

The first synthesis gas subsystem 14 and the second synthesis gas subsystem 16 generate synthesis gas. First synthesis gas subsystem 14 may be any of a number of types of subsystems for generating synthesis gas, such as a partial oxidation (POX) subsystem or steam reformer, or preferably, an autothermal refonner. Still another acceptable method for generating synthesis gas would be use of a plasma technique; for example, excess electrical energy from the system might be used with a steam reformer or POX with plasma. Other acceptable systems include gasification systems.

Gasification systems normally start with raw materials such as coal, petroleum based materials (crude oil, high sulfur fuel oil, petroleum coke, and other refinery residuals), gases, or materials that would otherwise be disposed of as waste. The feedstock is prepared and fed to the gasifier in either dry or slurried form where it reacts with steam and oxygen at high temperature and pressure in a reducing (oxygen starved) environment to make synthesis gas (mainly carbon monoxide and hydrogen). The high temperature and pressure in the gasifier convert the inorganic materials in the feedstock (such as ash and metals) into a vitrified material (slag) like course sand. Valuable metals may be concentrated and recovered for reuse from some feedstocks. The synthesis gas produced in gasifiers of this type are used on occasion as fuel for producing electricity, such as in an integrated gasification combined cycle (IGCC) power generation configuration. The combined cycle of an IGCC has a high efficiency gas turbine that bums synthesis gas to produce electricity.

One acceptable gasification process uses an entrained-bed, non-catalytic, partial oxidation process in which carbonaceous substances react at elevated temperatures and pressures to produce synthesis gas. Inorganic materials in the feed melt and are removed as a glass-like slag. Pressures and temperatures may be above 20 atmospheres and with temperatures between 2,200 F and 2,800 F. Slurred waste may be pumped to burners mounted at the top of a refractory-line gasifier. The feed, oxygen, and an auxiliary fuel, such as coal, react and are downwardly flowed through the gasifier to a quench chamber, which collects the slag. A lockhopper is eventually used to remove the slag. A scrubber cleans and further cools the resultant synthesis gas. The scrubber removes fine particulate matter which may be recycled to the gasifier. A sulfur recovery system may also be used in the gasification system. After the gasification process, the resultant synthesis gas can be delivered and used as described below. As noted above other systems may be used, and an autothermal reformer remains the preferred first synthesis gas subsystem.

First synthesis gas subsystem 14 has a compressed air inlet 28 that may be provided from an external source of compressed air 30, or from compressed air outlet 26 of turbine 12, or both. Light hydrocarbons (e.g., normally gaseous at standard temperature and pressure) such as methane are provided to the first synthesis gas subsystem through a first feedstock inlet 32. An embodiment of first synthesis gas subsystem 14, which includes an autothermal reformer, is described in more detail below in connection with FIG. 3. Subsystem 14 develops synthesis gas that is delivered to a first synthesis gas outlet 34.

Second synthesis gas subsystem 16 is preferably a steam reformer, but other substantially endothermic systems for generating synthesis gas (or that benefit from the transfer of thermal energy) may be used. As an important aspect to the present invention, the second synthesis gas subsystem 16 is thermally coupled to the turbine such that the thermal energy of the turbine exhaust is delivered to the second synthesis gas subsystem 16. In this example, the thermal coupling is accomplished by delivering the exhaust energy from turbine 12 to second synthesis gas subsystem 16. The thermal exhaust energy is shown delivered by exhaust outlet 22 and may be delivered by numerous types of heat exchange devices associated with the synthesis gas subsystem 16. The exhaust from the turbine delivered through conduit 22 exits the second synthesis gas subsystem 16 through conduit 23. Synthesis gas subsystem 16 has a second feedstock inlet 36 and a steam inlet 38. In the preferred embodiment, synthesis subsystem 16 is a steam reformer operating in the rang of 1000 to 1600 degrees Fahrenheit. Because the turbine exhaust 22 may not be sufficiently heated, a burner may be added that burns a tail gas or natural gas or both or other waste gases or liquids or combinations (see, e.g., burner 160 of FIG. 2). An embodiment of second synthesis gas subsystem 16, which includes a steam reformer, is described in more detail in connection with FIG. 4 below.

Subsystem 16 develops a synthesis gas that is delivered to second synthesis gas outlet 40. Outlets 34 and 40 deliver synthesis gas to conduit 42. Between synthesis gas subsystem 16 and conduit 42 may be a number of gas treatment devices for such things as the removal of a portion of the hydrogen as will be described further below. Synthesis gas within conduit 42 is delivered to synthesis subsystem 18.

Synthesis subsystem 18 receives synthesis gas from at least two sources (e.g., synthesis gas subsystems 14 and 16) and converts it to heavier hydrocarbons that are normally liquid or solid at standard temperature and pressure (but may also include gaseous products), and which may be referred to generally as a synthesis product. The liquid synthesis products are delivered through conduit 44 to storage 46 (or to a product upgrading unit). Synthesis subsystem 18 has a tail gas (low-BTU residue gas-typically below 100 BTU/scf when air is used) in offtake 48 and a water offtake 50. Tail gas produced by synthesis subsystem 18 and delivered to tail gas offtake 48 may be used elsewhere within system 10. For example, the tail gas may be used to provide or help provide reactive energy to second synthesis gas subsystem 16 or to a combustor, which is included as a part of turbine 12. Similarly, water from synthesis subsystem 18 delivered to water offtake 50 may be used elsewhere within system 10. For example, water may be used to generate steam for use with second synthesis gas subsystem 16.

Figure 2:
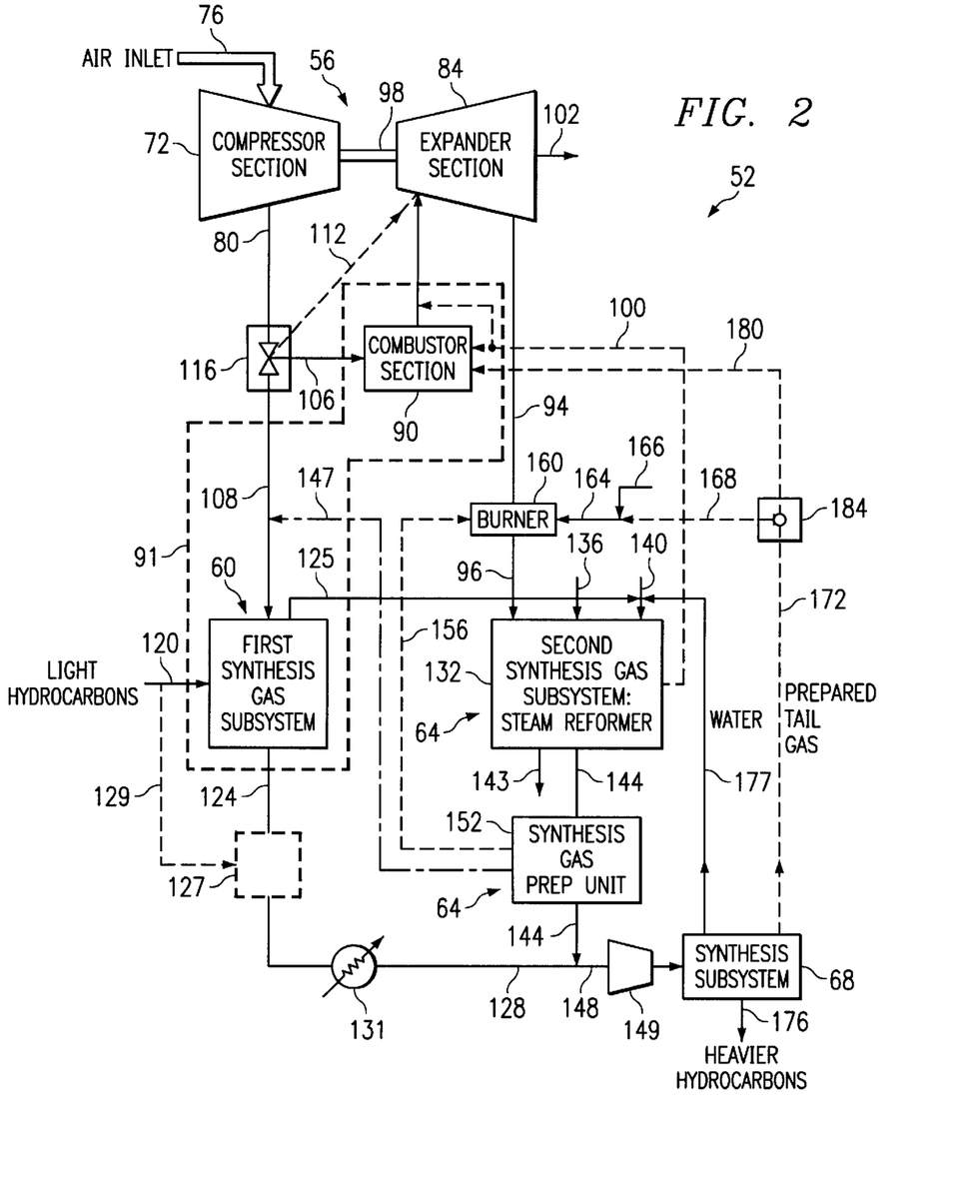
FIG. 2 is a schematic diagram of an embodiment of a conversion system according to another embodiment of the present invention.

Referring now to FIG. 2, another embodiment of a system 52 for converting normally gaseous, light hydrocarbons into heavier hydrocarbons is presented. System 52 includes a turbine 56; a first synthesis gas subsystem 60; a second synthesis gas subsystem 64, which preferably includes a steam reformer 132; and a synthesis subsystem 68.

Turbine 56 includes a compressor section 72 having an air inlet 76 and a compressor exhaust outlet 80. Compressor section 72 may include a number of compressors with components as is known in the art. Turbine 56 also includes an expander section 84 fluidly coupled to a combustor section 90, and having an expander exhaust outlet 94. Expander section 84 may include numerous expansion sections and components as is known in the art. Expander section 84 is preferably mechanically linked by linkage 98, such as a shaft, to compressor section 72. The net power generated by expander, or turbine, section 84, is depicted by power offtake 102. The net power generated, if any, may be used elsewhere in system 52 and/or be exported. Turbine 56 may be a gas turbine or may be a compressor/steam turbine combination.

Compressor exhaust in the form of compressed air from compressor section 72 is delivered into compressor exhaust outlet 80. The exhaust is delivered, at least in part, to combustor section 90 through conduit 106. In the embodiment shown, a portion may also be delivered through compressed air inlet 108 to first synthesis gas subsystem 60. In addition, a portion of the exhaust in outlet 80 may be delivered to expander section 84 by conduit 112 to assist with cooling of expander section 84. Thus, there may be a three-way split as shown at junction 116. It is to be understood that the components of the turbine/combustor/compressor may be included in a housing and are presented as such for illustrative reasons.

First synthesis gas subsystem 60 receives compressed air through an inlet, which may be from any source but preferably is from compressor exhaust 80 of turbine 56. In addition, first synthesis gas subsystem 60 receives light hydrocarbons, e.g., natural gas, from a first feedstock inlet 120. The light hydrocarbons may be preheated and conditioned before delivery to subsystem 60. Subsystem 60 produces a synthesis gas that is delivered to first synthesis gas outlet 124 preferably at about 1700–1800 degrees Fahrenheit. Synthesis gas subsystem 60 may have additional substances added, such as steam, to control the hydrogen to carbon monoxide ratio of the synthesis gas delivered to outlet 124. Water is typically created as a by-product and is preferably delivered by conduit 125 to the second synthesis gas subsystem 64. Conduit 125 may include a water treatment subsystem on part of it.

Synthesis gas subsystem 60 produces synthesis gas. Outlet 124 delivers the synthesis gas to a first portion of a synthesis gas conduit 128. A high steam pressure drum and other devices known in the art may be included as part of conduit 128. The hydrogen to carbon monoxide ratio is preferably about 2:1 (for cobalt-based catalyst, but other catalyst may be used with other ratios).

In an optional modification to system 52, a third synthesis gas subsystem 127, which is preferably a pressurized reformer, may be added downstream of first synthesis gas subsystem 60. The third synthesis gas subsystem 127 uses primarily the thermal energy of the synthesis gas from the first synthesis gas subsystem 60 to reform natural gas 129. Subsystem 127 may be what is referred to as a compact reformer. See, e.g., U.S. Pat. No. 5,980,840. The third synthesis gas subsystem 127 would deliver its synthesis gas to conduit 128 at about 1400 degrees. Conduit 128 may further contain a boiler. 131. Thus the synthesis gas from subsystem 60 (and optionally subsystem 127) is delivered to conduit 128.

Second synthesis gas subsystem 64 preferably includes a steam reformer 132. As an important aspect of the present invention, steam reformer 132 receives thermal exhaust energy from turbine 56 through exhaust conduit 94 and conduit 96. After transferring thermal energy to subsystem 64, the exhaust may be released through outlet 143. Steam reformer 132 receives light hydrocarbons through a second feedstock inlet 136. In addition, it receives steam/water through steam/water inlet 140. Steam reformer 132 preferably utilizes a steam reformer catalyst to convert the light hydrocarbons delivered through conduit 136 into synthesis gas that is delivered to second synthesis gas outlet 144, which preferably delivers it into synthesis gas preparation unit 152 and then to a portion of the synthesis gas conduit 148. Other synthesis gas generator types could be used, such as plasma synthesis gas generator. On conduit 144 between steam reformer 132 and the second portion of the synthesis gas conduit 148, there may be located a number of components that may be referred to as a synthesis gas preparation unit 152. Synthesis gas preparation unit 152 may include carbon dioxide removal devices and/or hydrogen removal devices. If a $CO_2$ removal device is included, the $CO_2$ may be transferred to the first synthesis gas system through conduit 147 to assist in adjusting the molar ratio (it may also be delivered to the second subsystem 64 and third subsystem 127). If a hydrogen removal device is included, the hydrogen removed may be used to assist with hydrocracking or hydro-treating elsewhere in system 52 or downstream from it, or may be used as fuel in a burner. As an example of the latter, hydrogen from synthesis gas preparation unit 152 may be delivered into conduit 156 and delivered to burner 160. $CO_2$ can also be removed from conduit 172 with a membrane and be delivered to one or more of the synthesis gas generators 60, 64, or 127 as feedstock to adjust the $H_2/CO$ ratio.

Exhaust from turbine 56, which is delivered through expander exhaust conduit 94 to conduit 96, may need to have its temperature increased to provide adequate feeding energy to the heat exchanger elements of steam reformer 132. Thus, duct burner 160 may be included for further heating the exhaust. Burner 160 has a fuel inlet 164. Fuel delivered through inlet 164 may be a hydrocarbon fuel feedstock delivered through conduit 166 or a low BTU residue gas, or tail gas, prepared as may be appropriate from synthesis subsystem 68 and delivered to inlet 164 through conduit 168 from tail gas outlet 172. Burner 160 thus may burn fuel from inlet 164 and/or hydrogen delivered through conduit 156. Exhaust gases from subsystem 64 may be delivered to combustor 90 or directly to expander section 84 by a return conduit 100.

Synthesis gas from first synthesis gas subsystem 60 is mixed with synthesis gas from second synthesis gas subsystem 64 in the synthesis gas conduit 128, 148. The combined synthesis gas is delivered to synthesis subsystem 68. A synthesis gas booster compressor 149 may be used to increase the pressure of the synthesis gas. Synthesis subsystem 68 may be, and preferably is, a Fischer-Tropsch system, as will be described in further detail in connection with FIG. 5. (it could also be other synthesis system such as methanol). Synthesis subsystem 68 produces a heavier, longer chain hydrocarbon product stream that is delivered to product outlet 176 where it may be delivered to storage and/or further processed.

Synthesis subsystem 68 also produces a low-BTU residual or tail gas (preferably $C_{<6}$ with 150 BTU/scf and more preferably 100 BTU/scf or lower) that is delivered to a tail gas outlet 172. Tail gas delivered to conduit 172 may be treated and prepared for use as fuel in either burner 160 or in combustor section 90. Conduit 172 delivers tail gas to conduit 168 and/or conduit 180. A control unit 184 (e.g., a valve system) may be optionally included at the junction between conduit 172, 168, and 180 to vary the portions of tail gas provided to conduits 168 and 180. Unit 184 can, by moving tail gas from the combustor (conduit 180) to the burner 160, allow for adjustments to the ratio of product to be obtained from synthesis subsystem 68 to the amount of electricity generated (off take 102). Water is made as a by-product in synthesis subsystem 68 and is preferably delivered by conduit 177 to steam/water inlet 140 of the second synthesis gas subsystem 64. Conduit 177 may include a water treatment subsystem to remove contaminants.

In an alternative embodiment, the reactor of first synthesis gas subsystem 60 may be combined with the combustor section 90 as shown by reference line 91. If, for example, the subsystem 60 includes an autothermal-reformer-reactor, the reactor and combustor may be combined with the combustor 90 to form a combined autothermal reformer combustor. In that case, substantially all the air from compressor section 72 is delivered to the autothermal-reformer-combustor where synthesis gas is prepared and all the exhaust (i.e., the synthesis gas) is delivered to the expander 84 (i.e., conduit 124 would be modified to deliver it to the expander 84). The synthesis gas that is exhausted from the turbine may then be used to assist with the thermal energy demands of the second synthesis gas subsystem before being delivered along with synthesis gas from the second synthesis gas subsystem to the synthesis subsystem. A booster compressor may be added to boost the synthesis gas from the first synthesis gas subsystem after it has exited the expander 84 and before the synthesis subsystem 68. See also FIG. 6 and the accompanying discussion below. A combined steam reformer combustor might also be used.

Figure 3:
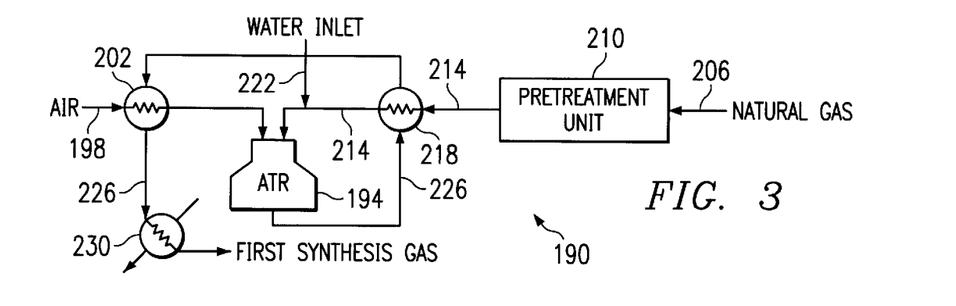
FIG. 3 is a schematic diagram of a first synthesis gas subsystem according to an aspect of the present invention.

Referring now to FIG. 3, one illustrative embodiment of a first synthesis gas subsystem 190 is presented. Subsystem 190 includes an autothermal reformer reactor (ATR) 194. Reactor 194 contains an appropriate catalyst, such as a nickel catalyst, as is known in the art. Subsystem 190 has an inlet 198. Inlet 198 may deliver air or enriched air (i.e., having an oxygen content greater than standard air) to ATR 194. Air inlet 198 is preferably preheated by heat exchanger 202.

Subsystem 190 has a first feedstock inlet 206 for receiving lighter hydrocarbons such as natural gas. Feedstock inlet 206 delivers the feedstock to a pretreatment unit 210. Unit 210 represents a number of components that may be used to treat the feedstock prior to delivery to ATR 194; for example, a separator, devices (such as an activated carbon vessel) for removing mecaptan sulfur, a device (such as a zinc oxide vessel) for removing $H_2S$, etc. Conduit 214 delivers the feedstock to ATR 194. Heat exchanger 218 may be included on conduit 214 to preheat the feedstock. A water inlet 222 may deliver water or steam or other substances into conduit 214 to help control hydrogen to carbon monoxide ratios within ATR 194. Autothermal reformer 194 produces a synthesis gas that is delivered into first synthesis gas outlet 226. Outlet 226 may be coupled to heat exchangers 218, 202 to provide heat energy to air (or enriched air) in conduit 198 and feedstock in conduit 214. Additional heat exchangers, such as heat exchanger 230, may be provided to adjust temperature of the synthesis gas within conduit 226 as desired. Synthesis gas within conduit 226 is delivered to a synthesis subsystem such as 18 in FIG. 1.

Figure 4:
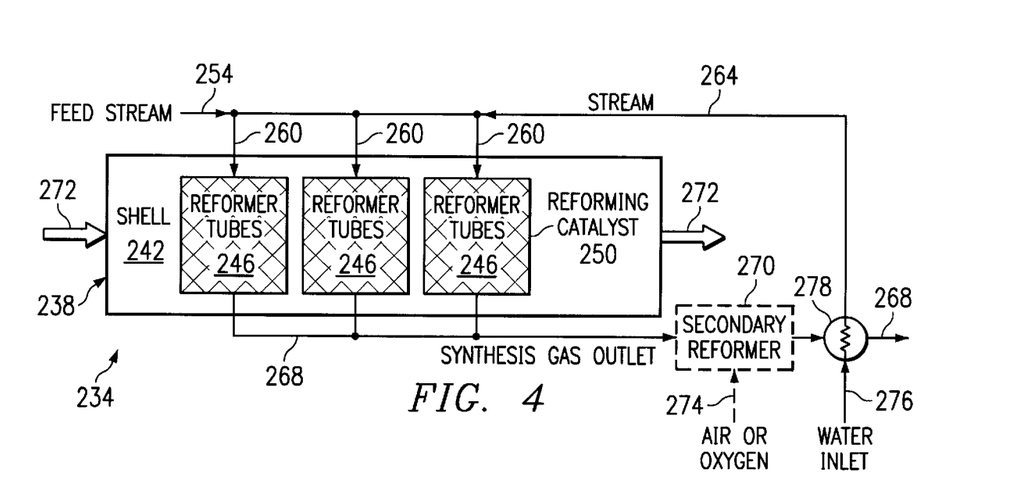
FIG. 4 is a schematic diagram of a second synthesis gas subsystem, which is a steam reformer, according to an aspect of the present invention.

Referring now to FIG. 4, one embodiment of a second synthesis gas subsystem 234 is presented. Subsystem 234 preferably includes a steam-reforming reactor 238. Steam reforming itself, the catalytic conversion of hydrocarbons by reaction with steam at elevated temperature, is known in the art. In this process, a fluid hydrocarbon, such as natural gas, is converted to a hot reformed gas mixture, or synthesis gas, containing hydrogen and carbon monoxide. The reaction may be generally represented as follows:

$$CH_4 + H_2O \rightarrow CO + 3H_2$$

This reaction is known generally as primary reforming and widely used in the production of synthesis gas or pure hydrogen. The primary reforming reaction is endothermic in nature, and the conventional operation is usually carried out by passing a gaseous mixture of fluid hydrocarbons and steam through an externally heated reaction tube or group of tubes. The tubes are packed with a suitable catalyst composition, such as solid catalyst granules deposited on an inert carrier material. The resulting reformed gas mixture discharges from said tubes as a hot reformer tube effluent from which heat may be recovered in a waste heat recovery zone. The hot reformer tube effluent from primary steam reforming is often passed directly to a secondary reforming zone. There the reformed gas mixture is passed, together with oxygen or air, through a bed of reforming catalyst so that the oxygen or air reacts with unconverted methane present in the reformed gas mixture. The gas mixture from such secondary reforming can then be cooled in a waste heat recovery zone prior to any further processing.

In the illustrative embodiment of FIG. 4, reactor 238 may include a shell 242 with a plurality of reformer tubes 246 within it. Tubes 246 are filled with a reforming catalyst 250, such as metals of Group VM of the periodic system having an atomic number not greater than 28 and/or oxides thereof and metals of the left-hand elements of Group VI and/or oxides thereof, which are known to be good reforming catalysts, or other catalysts known in the art. Other catalysts include, but are not limited to, nickel, nickel oxide, cobalt oxide, chromia, and molybdenum oxide. Promoters and treatments may be used as is known in the art. A promoted nickel oxide catalyst is preferred.

A feedstock inlet 254 delivers a feedstock of light hydrocarbons, such as natural gas, to tube inlets 260. The feedstock delivered to inlet 254 may be preheated. A steam inlet 264 provides steam to tube inlets 260 as well. The feedstock and steam delivered tubes 260 pass through the reforming catalyst contained within reformer tubes 246 to produce a synthesis gas which is delivered to second synthesis gas outlet 268. As known in the art, a secondary reformer, such as secondary reformer 270, may be included. Secondary reformer receives air or oxygen through inlet 274. Secondary reformer 270 typically contains a reforming catalyst to react the unconverted methane present in the reformed gas mixture introduced therein. The thermal energy of the synthesis gas in conduit 268 may be used to create the steam in conduit 264. For example, water may be delivered to water inlet 276 and steam produced in heat exchanger 278 and delivered into conduit 264.

The steam reforming reaction is endothermic and the necessary energy to sustain the reaction is provided by heated fluid or flue gas 272 passing over and about reformer tubes 246. A portion of the feedstock (i.e., light hydrocarbon and air) may also be delivered to shell 242 for combustion on the shell side of tubes 246. Heated fluid 272 is preferably provided in a substantial part by a turbine as discussed in connection with FIGS. 1 and 2—but a burner may also be used in further energize the fluid. The synthesis gas delivered to synthesis gas outlet 268 may then be delivered to a synthesis subsystem as previously described.

While subsystem 234 shows a single reforming zone and shows the use of reforming tubes, it is to be understood that numerous other embodiments may be used with the systems of FIGS. 1 and 2. For example, a fluidized bed may be used or a partial oxidation system.

In the embodiment of FIG. 4, the steam to hydrocarbon ratio will vary, as is known in the art, depending on the overall conditions employed in the primary reforming zone. The amount of steam employed is influenced by the requirement of avoiding carbon deposition on the catalyst and by the acceptable methane content of the effluent at the reforming conditions.

Many stream reforming operations are carried out in superatmospheric pressure conditions. Pressures between about 50 to about 800 p.s.i.g. are generally preferred.

Figure 5:
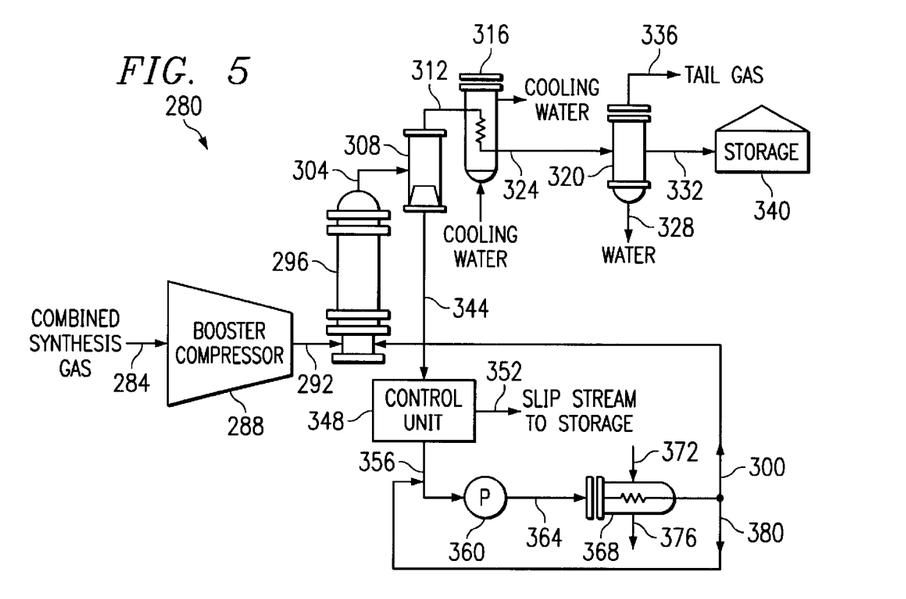
FIG. 5 is a schematic diagram of a synthesis subsystem according to an aspect of the present invention.

Referring now to FIG. 5, an illustrative embodiment of a synthesis subsystem 280 is presented that may be used as part of systems 10 (FIG. 1) or 52 (FIG. 2). In a preferred embodiment, subsystem 280 uses a Fischer-Tropsch reaction to convert synthesis gas into heavier hydrocarbons that are normally solids or liquids or gaseous at standard temperatures and pressures. Those skilled in the art will appreciate that numerous embodiments may be used to carry out such a reaction, and the one presented here is merely illustrative. It is possible to utilize other synthesis reactions as an aspect of the present invention.

Synthesis gas is delivered to subsystem 280 through a synthesis gas conduit 284. According to an important aspect of the present invention, the synthesis gas delivered to conduit 284 is synthesis gas combined from a plurality of synthesis gas subsystems as described previously in connection with FIGS. 1 and 2. It may be necessary in some situations to boost the pressure of the synthesis gas delivered to conduit 284. For this purpose, a booster compressor 288 may receive the synthesis gas, compress it, and deliver it to conduit 292. The energy to power booster compressor 288 may be provided by a turbine, such as turbine 56 in FIG. 2. Synthesis gas in conduit 292 is delivered to Fischer-Tropsch reactor 296.

Reactor 296 may take any of a number of forms known in the art, e.g., moving bed, fixed bed, etc., but as presented, is a form of a moving-bed reactor, having liquid circulated within it. Reactor 296 contains an appropriate Fischer-Tropsch catalyst, such as a cobalt-based, an iron-based, rhenium-based or a ruthenium-based case catalyst and may be supported on alumina, titania, or another inert support. The catalyst is ebullated within the reactor as gas and liquid are flowed up through the reactor. The heavy hydrocarbon liquid that is up-flowed is delivered through conduit 300. The gas and liquid product from reactor 296 is delivered through conduit 304 to separator 308, which separates the product into a gas effluent and a liquid effluent. The gas effluent is delivered through conduit 312, which is delivered to cooler 316. When cooled, some of the light hydrocarbons and water condense and the condensation products come out and go through conduit 324 to a cold separator 320. There, the water is removed and delivered into conduit 328, the liquid hydrocarbon product stream is removed and delivered to conduit 332, and a residual gas or tail gas is removed and delivered to conduit 336. The light liquid hydrocarbon products of conduit 332 may be delivered to storage 340 and/or to other units for further processing.

Returning now to separator 308, the liquid product, or ebullating oil, is delivered into conduit 344, which delivers it to a control unit 348. Control unit 348, according to the amount of ebullating oil within system 280, may send some of the ebullating oil to storage through a slip stream conduit 352 or to a recycle loop 356. Ebullating oil in the recycle loop 356 is delivered to a pump 360 which moves the ebullating oil through conduit 364 where it is delivered to heat exchanger 368. Heat exchanger 368 is used to adjust the temperature of the ebullating oil by adding or removing heat as necessary. The heat transfer fluid enters exchanger 368 at 372 and exits at 376. Ebullating oil from heat exchanger 368 is delivered in part through conduit 300 to Fischer-Tropsch reactor 296 as previously mentioned. Another portion is delivered through conduit 380 back to the suction side of pump 360 to keep a high velocity there as needed.

Figure 6:
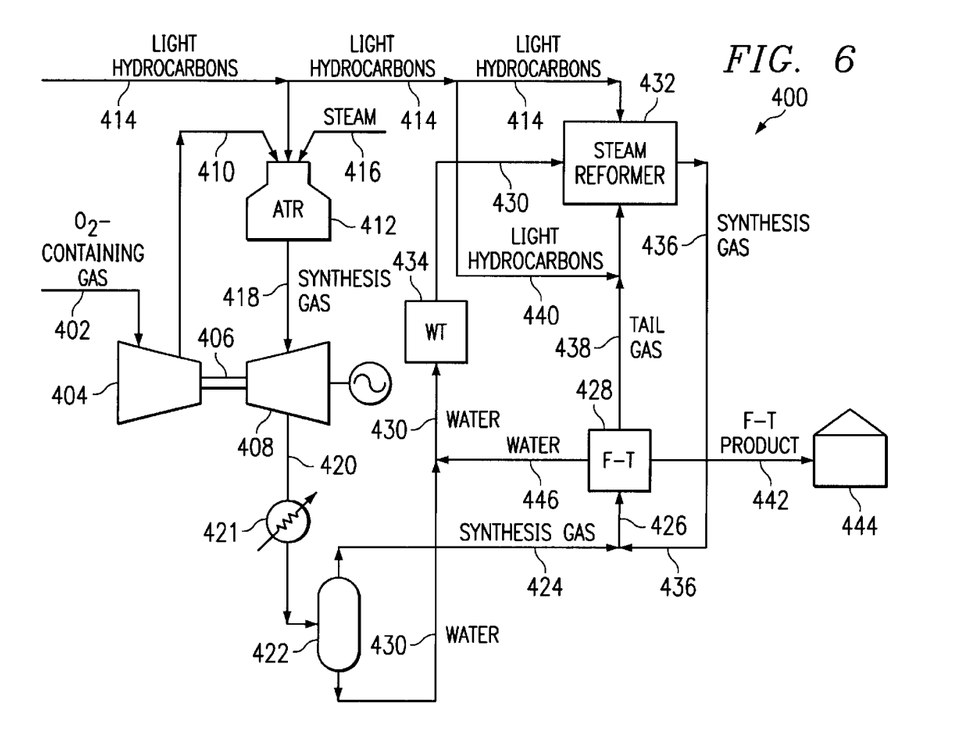
FIG. 6 is a schematic diagram of another embodiment of a system for converting light hydrocarbons to heavier hydrocarbons according to an aspect of the present invention.

Referring now to FIG. 6, another system 400 for converting ligher hydrocarbons to heavier hydrocarbons with a plurality of synthesis gas subsystems is shown. An important aspect of system 400 is that synthesis gas from a first synthesis gas subsystem 412 is delivered to an expander 408 before being delivered to a synthesis subsystem 428.

Air is introduced through conduit 402 to a compressor 404 (which may or may not be part of a steam turbine). The compressor is driven through mechanical linkage 406 that is powered by a turbine expander 408. Expander 408 may be a steam turbine or together with compressor 404 may be part of a gas turbine.

Compressor air from compressor 404 is delivered through conduit 410 to a first synthesis gas subsystem 412, which is preferably an autothermal reformer reactor. Light hydrocarbons, such as natural gas, are delivered through conduit 414 to the first synthesis gas subsystem 412. Steam may be delivered to first synthesis gas subsystem 412 through conduit 416 to help adjust the $CO:H_2$ ratio. With these feeds, first synthesis gas subsystem 412 generates a synthesis gas that is delivered by conduit 418 to expander 408. The expanding synthesis gas imparts mechanical energy that may be transmitted by linkage 406 to compressor 404 and any net energy may be exported.

The expanded synthesis gas is delivered by conduit 420 to condenser 421 and separator 422. The synthesis gas then continues through conduit 424 to conduit 426 and onto a synthesis subsystem 428, which is preferably a Fischer-Tropsch unit. Conduit 426 may include a synthesis gas booster compressor (like 149 in FIG. 2).

The by-product water knocked out at separator 422 is delivered by conduit 430 to a second synthesis gas subsystem 432. A water treatment subsystem 434 may be included on conduit 430 to remove any contaminants such as alcohols from it. Water treatment subsystem 434 may be a biological treatment system or a concentrator followed by a stripper tower unit.

Second synthesis gas subsystem 432 receives water through conduit 430 as previously noted, but also light hydrocarbons through conduit 414. The water/steam and light hydrocarbons are used to make synthesis gas that is delivered to conduit 436. Conduit 436 delivers the synthesis gas to conduit 426 from where it is introduced into synthesis subsystem 428. A low-BTU tail gas produced in the synthesis subsystem 428 is delivered by conduit 438 to second synthesis gas subsystem 432. Light hydrocarbons may also be introduced as needed into conduit 438 by conduit 440 to help supply the energy content thereof. The energy from the tail gas delivered into conduit 438 and/or the light hydrocarbons delivered through conduit 440 may fuel burners within second synthesis gas subsystem 432, which is preferably a steam reformer.

Synthesis subsystem 428 produces heavier hydrocarbons such as those mentioned further below and delivers them to one or more conduits such as conduit 442 from where they may go to storage, e.g, 444, or for downstream processing. Synthesis subsystem 428 is preferably subsystem that uses a Fischer-Tropsch reaction to convert synthesis gas to heavier hydrocarbons. By-product water may also be produced and is delivered to conduit 446, which is preferably fluidly coupled to conduit 430.

The systems and methods of the present invention are preferably used to convert synthesis gas into heavier, longer-chain hydrocarbons, e.g., the full spectrum of $C_{5+}$ products through the Fischer-Tropsch reaction (but other reactions might be used in some situations). The heavier Fischer-Tropsch products that may be made directly or with downstream processing include numerous products for numerous uses. Furthermore, a number changes may be anticipated as the system is applied in different environments. A number of examples of each are presented below.

The Fischer-Tropsch products may include synthetic alpha olefins adapted for many applications, including, without limitation, PAO feedstock (alpha olefins in the range of $C_6$ to $C_{12}$ and preferably $C_{10}$ are used to produce poly alpha olefins); alpha olefins for laundry and other detergents (preferably $C_{12}$–$C_{16}$); chlorination stock to be used in textiles, pharmaceuticals and transportation lubricants/hydraulic fluids (preferably $C_{18}$–$C_{24}$); alpha olefins used to produce particle board emulsions and poly vinyl chloride lubricants ($C_{24}$–$C_{28}$); and alpha olefins used to manufacture decorative and industrial candles, particle board emulsions and PVC lubricants ($C_{30}$+ alpha olefins, which are considered a synthetic paraffin wax and therefore used in many of the markets where paraffin waxes are used). The Fischer-Tropsch products are also well suited for use as synthetic white oils because Fischer-Tropsch liquid normal paraffins meet FDA specifications governing their use in direct food contact applications, which gives them a wide range of potential markets to enter, including markets which traditionally use food grade mineral oils. Similarly, the Fischer-Tropsch product may be used for technical grade mineral or white oils that are used to produce paints, stains and inks, among other end-use products and may be used as a pharmaceutical (USP) grade white oil to be used to produce cosmetics and healthcare products. In these applications, Fischer-Tropsch products are better because the liquid or hydroisomerized product can probably satisfy ASTM standards with little effort.

The Fischer-Tropsch products may also be used for synthetic liquid n-paraffins in numerous applications. The Fischer-Tropch product may be used as a chlorination feedstock to be used, for example, to produce chlorinated normal paraffins for use in textiles and industrial lubricants. The product may also be used as a linear alkyl benzene (LAB) feedstock ($C_{10}$ to $C_{13}$) which may be used for laundry detergents. The Fischer-Tropsch product may also be used as an aluminum rolling oil ($C_{14}$ to $C_{17}$), e.g., for cold rolling oils for aluminum foil. Further the Fischer-Tropsch product N-paraffin may be used for "liquid" candles.

The Fischer-Tropsch product may be used as a synthetic wax in numerous applications. For example, the product may be used to make thermostat wax, which is used primarily to control automobile thermostats. The wax is particularly suitable for this since it must be uniform in molecular weight, carbon number distribution and molecular structure. The Fischer-Tropsch wax may be used to make hotmelt adhesives, i.e., used as a viscosity modifier for industrial hotmelt adhesives. The synthetic wax may be used in printing inks. In that case, the wax is used as an antiscuff surface modifier for fine grade web offset and gravure inks. It may also be used for paints and stains. The wax is used to enhance water repellency of water-based paints and stains. The Fischer-Tropsch product may be used to make corrugated board in which the waxes are used to add strength and water repellency to the corrugated board. Similarly, the Fischer-Tropsch product may also be used as a wax for packaging and food additives.

The synthetic wax may be used as a PVC lubricant/extrusion aid; the high melting point waxes are used as internal/external lubricants for PVC extrusion. The wax may be used as a flushing compound, to impart the dripless quality to decorative candles, with cosmetics as a viscosity modifier and melting point enhancer, to bind various drugs which are in powdered form into tablet form (they also impart a slippery surface to tablets such as aspirin, etc.). Waxy Fischer-Tropsch products may also be used as plasticizers and extrusion aids for various plastics such as high density polyethylene, PET linear low density polyethylene and polypropylene. Another use is as anti-ozone additives to protect the outside surfaces of rubber products from packing and ozone damages.

Fischer-Tropsch product in the form of synthetic lubricants may be used in numerous additional applications. For example, the synthetic lubricants may be used as environmentally friendly drilling fluids. Fischer-Tropsch oils may be used to produce highly stable high temperature operation automatic transmission fluids. They may also be used as a hydraulic fluid that is very stable at high temperatures and ideally suited for use in vehicular and industrial hydraulic compounds. The synthetic lubricants may also be used as vehicular lubricants (PCMO and HDD). The Fischer-Tropsch product in the form of a synthetic lubricant may be used as a quenching oil or cutting oil. Further they may be used for a plurality of specialty lubricants such as for two-cycle, marine lubricants, or baroil. They may also be used as a vehicle for lubricant-additives.

An exciting aspect of the products that may be made from or as part of the Fischer-Tropsch products are synthetic fuels and blends, including Fischer-Tropsch compression ignition fuels, Fischer-Tropsch spark ignition fuels, feedstocks for fuel cells, aviation fuel (turbine and spark-ignition) and railroad fuels. The sulfur-free clean nature of the synthetic fuels thus made are advantageous.

The Fischer-Tropsch products may also be used as synthetic solvents. As such, the uses of the synthetic solvents include as printing inks, paints, stains, drying agents, dye transfer agents, synthetic heptane, hexane, and de-waxing agents.

The process, such as that presented in connection with the figures, may be adapted with other plants for additional purposes and may also be modified for application in the various environments throughout the world. Fischer-Tropsch plants can be built in a number of different settings, which will, by definition, determine some of the plant characteristics. The following is a list of some of the settings in which Fischer-Tropsch plants may be applied. The character of these plants will be controlled by factors including weather conditions, specifically whether it is tropical or temperate, or arctic settings, as well as local conditions, such as wind, wave action, altitude and precipitation.

Land-based plants imply the absence of water, and can have permanent or temporary foundations. Sites will range from sea level to elevations limited by turbine capability. Further adjustments are made for certain plant conditions such as arctic weather conditions on the North Slope. Riverine/Deltaic Fischer-Tropsch plants generally are capable of accommodating fluctuating water levels due to flood conditions, consolidated soil, regional subsidence, and other dynamic conditions common to this setting. Intratidal Fischer-Tropsch plants include many of the same conditions as Riverine/Deltaic Fischer-Tropsch plants, but also include design consideration known in the art for tides and wave motion. Open water Fischer-Tropsch plants are engineered to accommodate wind and waves motions found in open marine conditions.

Numerous platform options are available for Fischer-Tropsch plants to help accommodate their application in the various settings and conditions. The following listing is a brief characterization of bases or platforms on Fischer-Tropsch plants may be mounted. A barge-mounted Fischer-Tropsch plant may be used in marine, intratidal, and Deltaic/Riverine settings. The Fischer-Tropsch plants may be made from material ranging from metal to concrete. A plant may be mounted on a ship primarily for an open marine condition (s), and may be utilized under conditions similar to oil production from ships today. The plants may be modular (e.g., steel skid-mounted containers). These modular Fischer-Tropsch plants are subdivided into modules on steel skid-mounted containers for efficient transport, setup, connect and disconnect. Modular Fischer-Tropsch plants may range in sizes from small enough for shipment by rail to large enough to be carried as a heavy lift from a barge or ship. The plants may also be spar/offshore platform mounted Fischer-Tropsch plants. These Fischer-Tropsch plants are mounted on offshore and open marine settings spar or platforms, either retrofitted onto platforms that were previously designed for offshore oil and gas production or on platforms built specifically for the Fischer-Tropsch plant. The Fischer-Tropsch plant on a vessel may also be modified for use in recovering and converting hydrates from the ocean floor. These are but a few examples.

In addition to these platforms and settings, the plants may be oriented toward numerous other or additional applications. For example, the plant may be an aspect of a desalination plant. These Fischer-Tropsch plants are designed to use Fischer-Tropsch process heat (the Fischer-Tropsch and syngas reactions) to convert available water into water suitable for agriculture, industrial or portable water. The desalination may be by reverse osmosis or thermal desalination.

Although the present invention and its advantages have been described in detail, it should be understood that various changes, substitutions and alterations can be made therein without departing from the spirit and scope of the invention as defined by the appended claims. For example, while FIG. 5 presents one embodiment of a synthesis subsystem, numerous embodiments of such subsystems are possible, including those shown in U.S. Pat. No. 4,973,453, which is incorporated herein by reference for all purposes. As another example, components and subsystems shown in one embodiment may be used in other embodiments; as a specific example of this, the CO2 recycle 147 mentioned in FIG. 2 may be practiced with all the embodiments.

What is claimed is:

1. A method for converting normally gaseous hydrocarbons into heavier hydrocarbons that are normally solid or liquid at standard temperature and pressure, the method comprising the steps of:

preparing a synthesis gas in a first synthesis gas generator;

preparing a synthesis gas in a second synthesis gas generator that is a steam reformer;

delivering thermal energy from a turbine to the steam reformer;

delivering the synthesis gas from the first synthesis gas generator and the steam reformer to a Fischer-Tropsch unit; and converting synthesis gas to heavier hydrocarbons in the Fischer- Tropsch unit.

2. The method of claim 1 wherein the first synthesis gas generator is an autothermal reformer and further comprising the steps of:

compressing air with a compressor, delivering the compressed air from the compressor to the autothermal reformer;

combusting a fuel in a combustor with air;

expanding gases from the combustor in an expander; and transmitting energy from the expander to the steam reformer to provide at least a portion of the energy required therein for conversion of feedstocks to synthesis gas.

3. The method of claim further comprising the step of disposing of wastewater by using it in the steam reformer.

4. The method of claim 1 further comprising the step of.
preparing a synthesis gas in a third synthesis gas generator that is thermally coupled to the first synthesis gas generator; and
delivering the synthesis gas from the third synthesis gas generator to the Fischer-Tropsch unit.

5. A method for converting light hydrocarbons into heavier hydrocarbons ($C_{5+}$), the method comprising the steps of:
using a turbine, which has a compressor, combustor, and expander, to prepare a compressed oxygen-containing gas stream;
delivering the compressed oxygen-containing gas stream to a first synthesis gas generator;
using the first synthesis gas generator to prepare a first synthesis gas;
using a steam methane reformer to prepare a second synthesis gas;
delivering the first synthesis gas and the second synthesis gas to a Fischer-Tropsch reactor to produce the heavier hydrocarbons and a tail gas;
delivering the tail gas to the turbine combustor for use as a fuel in the combustor; and
delivering exhaust heat from the turbine expander to the steam methane reformer to assist in the production of the second synthesis gas.

* * * * *